United States Patent [19]

Okumura

[11] Patent Number: 5,270,749
[45] Date of Patent: Dec. 14, 1993

[54] OPTHALMIC APPARATUS FOR MEASURING THE REFRACTIVE POWER OF A LENS

[75] Inventor: Toshiaki Okumura, Yokohama, Japan

[73] Assignee: Canon Kabushiki Kaisha, Tokyo, Japan

[21] Appl. No.: 798,947

[22] Filed: Nov. 27, 1991

[30] Foreign Application Priority Data

Nov. 29, 1990 [JP] Japan ................................. 2-336727

[51] Int. Cl.$^5$ .............................................. A61B 3/10
[52] U.S. Cl. ..................... 351/211; 351/205; 351/214; 351/221
[58] Field of Search ............... 351/205, 211, 214, 221, 351/237

[56] References Cited

U.S. PATENT DOCUMENTS 4,861,154 8/1989 Sherwin et al. ..................... 351/211
4,929,076 5/1990 Masuda et al. .

Primary Examiner—Rodney B. Bovernick
Assistant Examiner—Hung Xuan Dang
Attorney, Agent, or Firm—Fitzpatrick, Cella, Harper & Scinto

[57] ABSTRACT

An ophthalmic apparatus has a diopter adjustment which adjusts the diopter of a target presented to an eye under test based on measurement of the refractive index of a lens put on the eye under test so that the diopter of the target matches the diopter of the eye under test.

6 Claims, 5 Drawing Sheets

OPTHALMIC APPARATUS FOR MEASURING THE REFRACTIVE POWER OF A LENS

BACKGROUND OF THE INVENTION

1. Field of the Invention

The present invention relates to an ophthalmic apparatus such as an eye-refractometer used in an ophthalmic hospital.

2. Related Background Art

A prior art ophthalmic apparatus such as an eye-refractometer has a diopter inducing optical system to induce a refractive power of an eye under test to a far point by changing the diopter of a target in order to permit accurate measurement. In such an apparatus, the position of the target is always constant prior to the inducement and a standard diopter of the diopter inducing system is set to essentially fit to a emmetropic eye.

However, in the prior art apparatus, if the eye under test is emmetropic, it can easily recognize the initially set target and the inducement can be immediately started, but if the eye under test is myopic or hyperopic, it is hard to recognize the target. Accordingly it is necessary to first measure, the refractive power of the eye and reinitialize the diopter of the target based on the refractive power of the eye. Thus, a time band during which the eye under test cannot clearly recognize the target is included and the measurement time is long.

U.S. Pat. No. 4,929,076 discloses the adjustment of the diopter of a fixed target when the curvature of a cornea is measured, in accordance with the measurement of the refractive power of the eye but it is different from the idea of this invention of eliminating the time band during which the eye under test cannot clearly recognize the fixation target in the initial stage of the measurement.

In the past, the refractive power of an eye-glass lens and a refractive power of an eye have been sequentially measured by separate apparatus in an eye-glass shop. Thus, if the eye under test has myopia or is hyperopic, a time band during which the eye under test cannot clearly recognize the fixation target is included in the initial stage of the measurement of a refractive power of the eye.

SUMMARY OF THE INVENTION

It is an object of the present invention to provide an ophthalmic apparatus which eliminates the time band during which an eye under test cannot clearly recognize a fixation target in an initial stage of measurement or test.

It is another object of the present invention to provide an ophthalmic apparatus which initializes the diopter of a target to fit to an eye under test when the eye under test does not suffer emmetropia in order to shorten the measurement time.

DETAILED DESCRIPTION OF THE PREFERRED EMBODIMENTS

Figure 1:
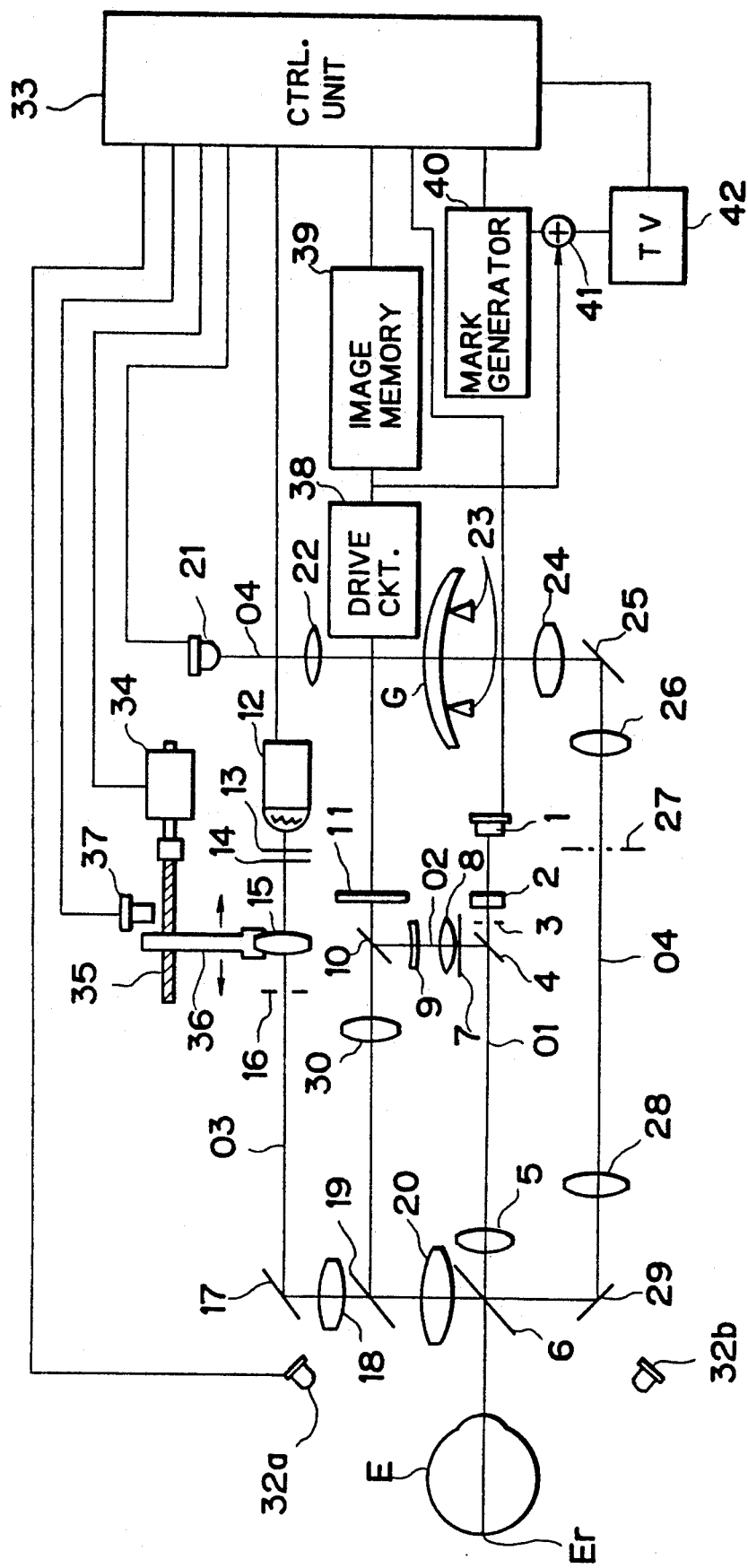
FIG. 1 shows a configuration of a first embodiment of the present invention.
Figure 2:
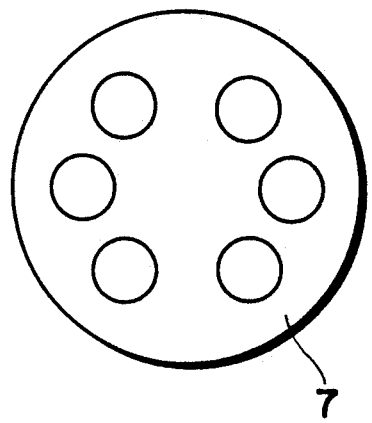
FIGS. 2 and 3 show front views of splitting prisms.
Figure 3:
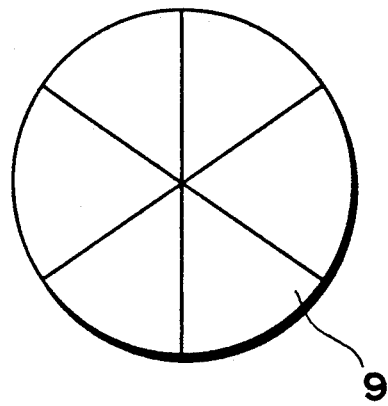
Figure 4:
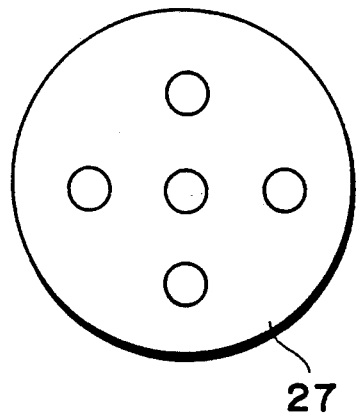
FIG. 4 shows a front view of an iris.
Figure 5:
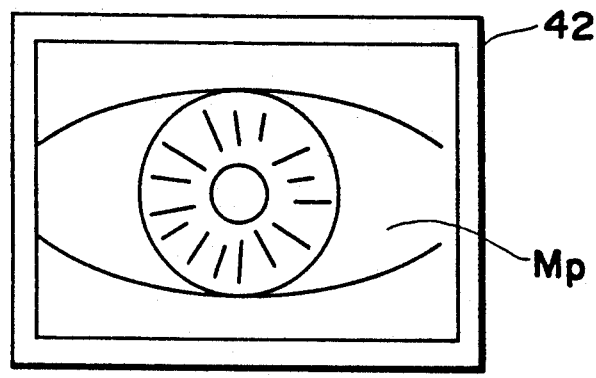
FIG. 5 shows a front view of an eye-front image on a television monitor.

FIG. 1 shows a configuration of an embodiment of the present invention in which the present invention is applied to an eye-refractometer. Arranged on a light path 01 from a light source 1 for measuring an eye refractive power to an eye E under test are a lens 2, an iris 3, a center-apertured mirror 4, a lens 5 and a dichroic mirror 6. Arranged on a reflection light path 02 of the apertured mirror 4 are an iris 7 having six apertures as shown in FIG. 2, a splitting prism 9 comprising six wedge prisms as shown in FIG. 3 and a dichroic mirror 10. Those elements form an eye-refractometer. Arranged on a light path 03 from a light source 12 for illuminating a target to the eye E under test are a diffusion plate 13, a fixation target 14, a lens 15 movable along the light path 03, that is, along an arrow shown in FIG. 1 by drive means to be described later, an iris 16, a total reflection mirror 17, a lens 18, a half-mirror and a lens 20. These elements together with the dichroic mirror 6 form a diopter inducing optical system. Arranged on a light path 04 from a light source 21 for measuring a refractive power of a lens to the dichroic mirror 6 are a lens 22, an abutment 23 for a lens under test, a lens 24, a total reflection mirror 25, a lens 26, an iris 27 having five apertures as shown in FIG. 5, a lens 28, a total reflection mirror 29 and the dichroic mirror 6, and arranged on the reflection path of the half-mirror 19 are a lens 30 and the dichronic mirror 10. Those elements form a portion of a lens refractometer. Eye-front illumination light sources 32a and 32b are arranged obliquely to the eye E under test.

On the other hand, control means 33 for controlling those optical systems is provided and the outputs of the control means 33 are supplied to the eye-refractometer light source 1, the target illumination light source 12, the lens refractometer light source 21 and the eye-front illumination light sources 32a and 32b. The output of the control means 33 is also supplied to a lens drive motor 34 to drive the lens 15. A lens mount 36 having the lens 15 fixed thereto is mounted on a lens feed rod 35 fixed to a shaft of the lens drive motor 34 so that the lens 15 is moved along the optical axis as the lens drive motor 34 rotates. A lens position detector 37 having an output thereof connected to the control means 33 is arranged in the vicinity of the lens feed rod 35 to enable the detection of the position of the lens 15. An output of the image pickup device 11 is supplied to an image pickup device driver 38, an output of the image pickup device driver 38 is supplied to image memory means 39, and an output of the image memory means is supplied to the control means 33. The output of the control means 33 is supplied to mark generation means 40, the outputs of the image pickup device driver 38 and the mark generation means 40 are supplied to image synthesizing means 41, and an output of the image synthesizing means 41 is supplied to a TV monitor 42.

The wavelengths of the light beams of the eye-refractometer light source 1, the target illumination light source 12, the lens refractometer light source 21 and the eye-front illumination light sources 32a and 32b are separated from each other and they have such wavelength spectrography that the dichroic mirror 6 transmits the light beams from the eye refractometering light source 1 and the lens refractometer light source 21 and reflects the light beams from the target illumination light source 12 and the eye-front illumination light sources 32a and 32b, and the dichroic mirror 10 transmits the light beams from the lens refractometer light source 21 and the eye-front illumination light sources 32a and 32b and reflects the light beam from the eye refractometer light source 1.

When the eye-front illumination light sources 32a and 32b are turned on, the light beams thereof illuminate the eye-front of the eye E under test, and the eye-front image is reflected by the dichroic mirror 6, passes through the lens 20, is reflected by the half-mirror 19 and focused on the image pickup device 11 through the lens 30 and the dichroic mirror 10. The eye-front image is supplied to the TV monitor 42 by the image pickup device driver 38 as shown in FIG. 5 so that an operator aligns the light beam by watching the image. On the other hand, the light beam from the target illumination light source 12 is diffused by the diffusion plate 13 to illuminate the fixation target 14 from the back, and it passes through the lens 15 and the iris 16, is reflected by the total reflection mirror 17, passes through the lens 18, the half-mirror 19 and the lens 20, is reflected by the dichroic mirror 6 and reaches the eye E under test The diopter of the target 14 is set by the position of the lens 15. When the eye E under test suffers emmetropia, the lens 15 is positioned at the initial set position and the target 14 is displayed to make the eye E under test to fix to the target 14. Then, the lens 15 is moved to induce the refractive power of the eye E under test to a far point.

Figure 6:
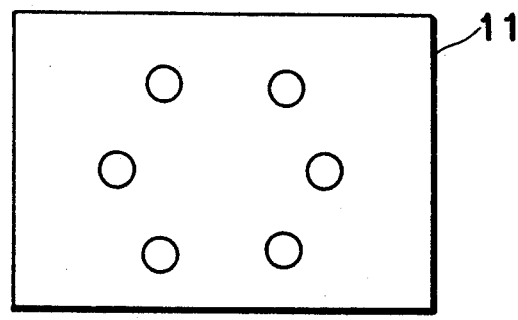
FIG. 6 shows a reflected image of an eye-bottom on an image pickup device.

After the inducement, the eye-front illumination light sources 32a and 32b are turned off and the eye refractometer light source 1 is turned on. Thus, the light beam travels on the light path 01, passes through the lens 2, the iris 3, the aperture of the apertured mirror 4, the lens 5 and the dichroic mirror 6 and reaches the eye-bottom Er of the eye E under test. The eye-bottom reflected light beam returns along the same light path, is reflected by the apertured mirror 4, passes through the iris 7 and the lens 8, is split from the optical axis by the splitting prism 9, and is reflected by the dichroic mirror 10. Thus, six images are formed on the image pickup device 11 as shown in FIG. 6. Those images are outputted by the image pickup device driver 38 as video signals, and stored in the image memory means 39 and also outputted to the TV monitor 42 through the image synthesizing means 41. The eye refractive power is calculated by the control means 33 based on the positional relationship of those images stored in the image memory means 39.

The above procedure is for the measurement of emmetropia when the eye E under test does not put the eye-glasses lens G. When the eye E under test puts on the eye-glasses lens G, the refractive power of the lens G is first measured and the position of the lens 15 is displaced from the initial set position in accordance with the measurement of the refractive power so that the eye E under test can recognize the target 14. The inducement starts from the displaced position. The subsequent process for the eye refractometering is same as that described above.

Figure 7:
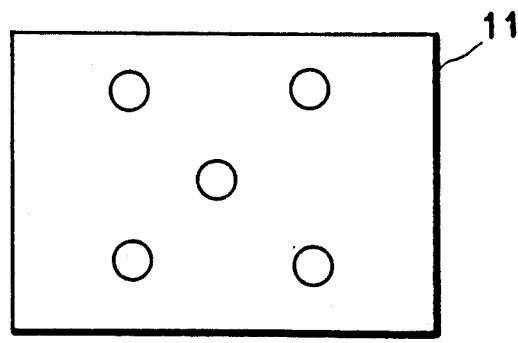
FIG. 7 shows a transmitted light flux image of a lens on the image pickup device.

In the refraction measurement of the eye-glasses lens G, the lens G abuts against the lens abutment 23 and is arranged on the light path 04, and then the lens refractometer light source 21 is turned on. The light beam travels along the light path 04, passes through the lens 22, the eye-glasses lens G and the lens 24, is reflected by the total reflection mirror 25, passes through the lens 26, the iris 27 and the lens 28, is reflected by the total reflection mirror 25, passes through the lens 26, the iris 27 and the lens 28, is reflected by the total reflection mirror 29, passes through the dichroic mirror 6 and the lens 20, is reflected by the half-mirror 19, and passes through the lens 30 and the dichroic mirror 10. Thus, five images are formed on the image pickup device 11 as shown in FIG. 7. The refractive power of the eye-glasses lens G is calculated based on the positional relationship of those images, as is the eye refractive power. The control means 33 displaces the lens 15 through the lens drive motor 34 based on the measurement. The measurement data of the eye-glasses lens G is stored in the memory means (for example, built in the control means 33) so that the measurement data may be used when the eye refractive power is measured at a later stage.

In the alignment process, the mark generated by the mark generation means 40 is combined with the eye-front image Mp by the image synthesizing means 41 and it may be displayed on the TV monitor 42 to facilitate the alignment.

In the ophthalmic apparatus of the present embodiment, when the eye refractive power is to be measured, the lens refractive power is measured by the lens refractometer and the diopter of the target is initially adjusted in accordance with the refractive power so that it fits to the eye under test, and then the inducement of the diopter of the eye under test is started. Accordingly, even if the eye under test does not suffer emmetropia, it can fixedly view the target and the inducement can be immediately started. Thus, the time required for the inducement, that is the measurement time is shortened.

Figure 8:
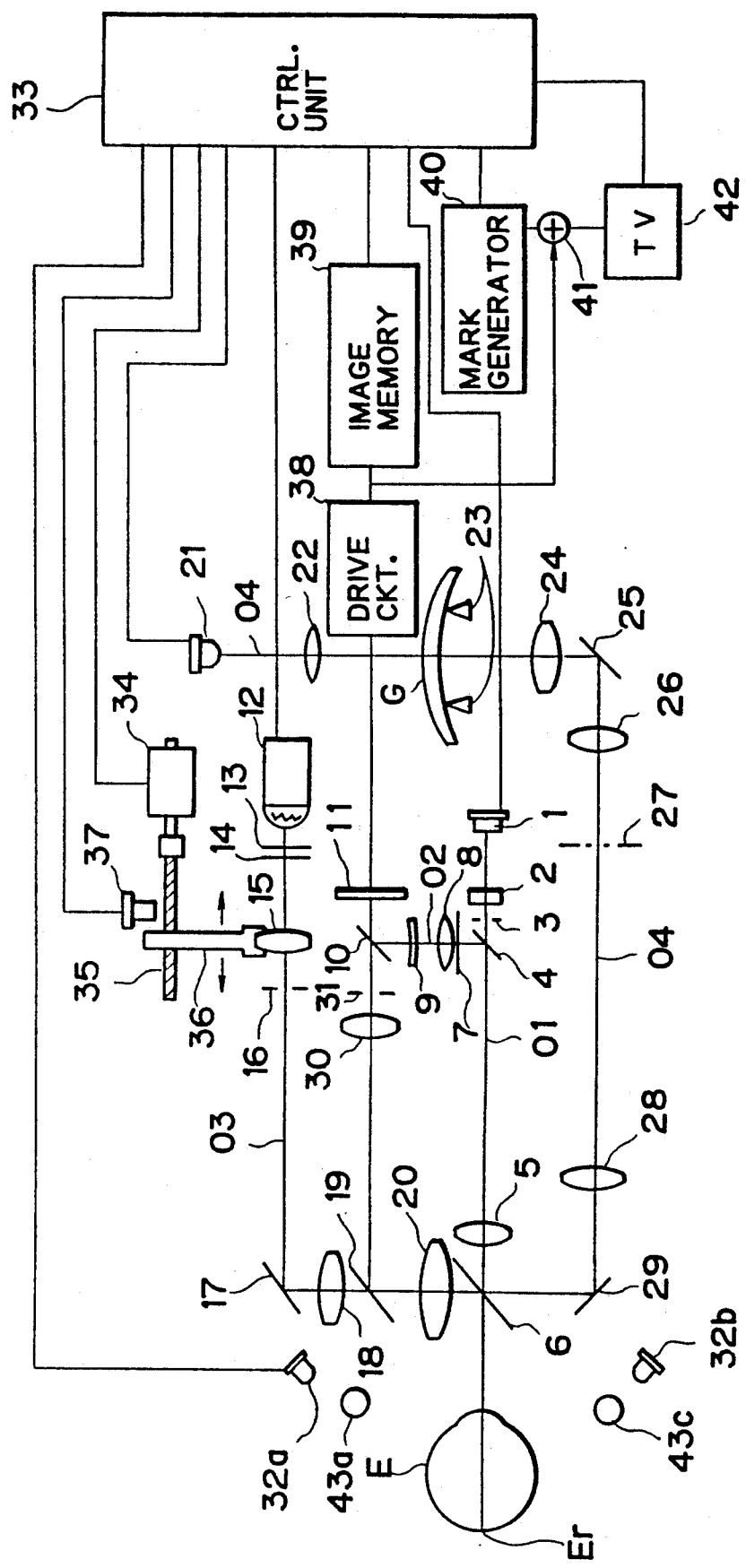
FIG. 8 shows a configuration of another embodiment.
Figure 9:
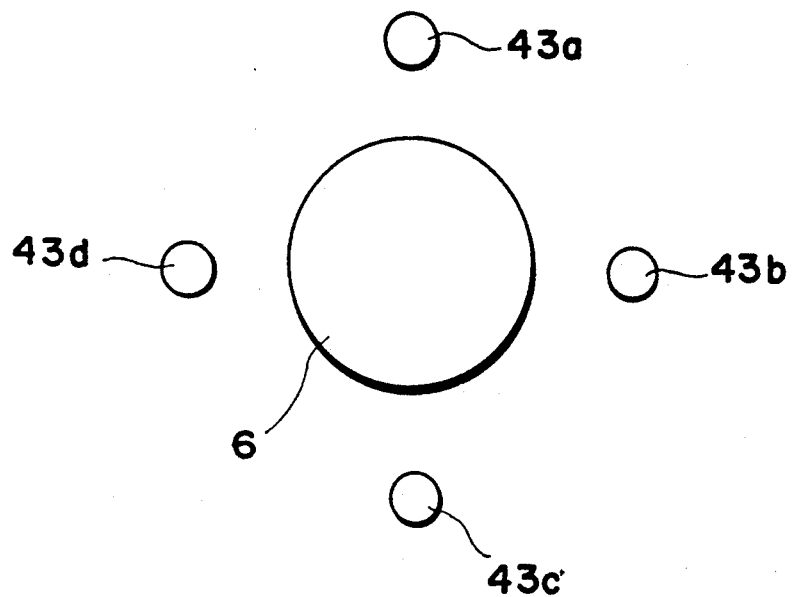
FIG. 9 shows a front view of an arrangement of a light source for measuring a shape of a cornea.

FIG. 8 shows a configuration of another embodiment in which cornea shape measurement means is added to the first embodiment. As shown in FIG. 9 which is a front view as viewed from the eye E under test, four cornea shape measuring light sources 43a–43d are arranged symmetrically around the optical axis around the dichroic mirror 6 to face the eye E under test. Although not shown, the light sources 43a–43d are connected to the control means 33. The configuration is identical to that of the first embodiment except that an iris 31 is inserted between the lens 30 and the dichroic mirror 10.

Figure 10:
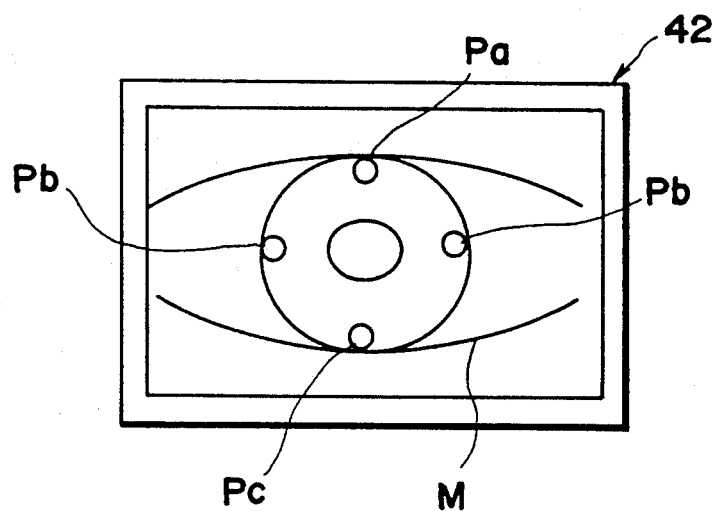
FIG. 10 shows an eye-front image and a cornea reflected image on the TV monitor.

In the measurement of the cornea shape, when the cornea shape measuring light sources 43a–43d are turned on, the light beams reach the eye E under test and the cornea reflected images are focused on the image pickup device 11 through the same light path as that of the eye-front image in the first embodiment, and the cornea shape is calculated by the control means 33 based on the positional relationship of the images. Other operational processes are same as that of the first embodiment. The cornea reflected images Pa - Pd together with the eye-front image M may be displayed on the TV monitor 42 as shown in FIG. 10.

In the embodiment of FIG. 8, when the eye refractive power is measured first and the cornea shape is measured later, the initial adjustment of the diopter of the target is identical to that of the first embodiment. When the cornea shape is measured first and the eye refractive power is measured later, the diopter of the target may be adjusted based on the measurement of the lens refractive power so that the eye under test is made to watch the target from the initial stage of the measurement in order to attain the rapid measurement.

The lens in the present invention is not limited to use with eye-glasses lens but it may be used with a contact lens.

The present invention is applicable to an ophthalmic apparatus having an eye-fundus camera or an eye-fundus check function. It adjusts the diopter of the target based on the measurement of the refractive power of the lens so that the eye under test is made to watch the target from the initial stage of the eye-fundus check to attain the quick eye-fundus test.

What is claimed is:

1. An ophthalmic apparatus, comprising:
a lens measuring system for measuring a refractive power of a lens for an eye under test;
an information obtaining system for obtaining ophthalmic information of the eye under test;
a visual target presented to the eye under test when the ophthalmic information of the eye under test is obtained, said visual target being projected on the eye under test by an optical system; and
adjusting means for adjusting a focus condition of the optical system with respect to the visual target on the basis of the refractive power of the lens measured by said lens measuring system.

2. An ophthalmic apparatus according to claim 1 wherein said information obtaining system is an eye refraction system.

3. An ophthalmic apparatus according to claim 1 wherein said information obtaining system is a cornea shape measuring system.

4. A refractometer, comprising:
a lens measuring system for measuring a refractive power of a lens for an eye under test;
an eye refraction measuring system for measuring a refractive power of the eye under test;
an inducing system having an optical system for projecting a visual target on the eye under test when the refractive power of the eye under test is measured, a focus condition of said optical system with respect to the visual target being variable; and
adjusting means for adjusting said focus condition of said optical system with respect to the visual target on the basis of the lens refractive power measured by said lens measuring system.

5. A refractometer, comprising:
memory means for storing measurement data for a refractive power of a lens for an eye under test;
an information obtaining system for obtaining ophthalmic information of the eye under test;
an inducing system having an optical system for projecting a visual target presented to the eye under test when the ophthalmic information is obtained, a focus condition of said optical system with respect to the visual target being variable; and
adjusting means for adjusting the focus condition of said optical system with respect to the visual target on the basis of the lens refractive power stored in said memory means.

6. An ophthalmic apparatus, comprising:
memory means for storing measurement data for a refractive power of a lens for an eye under test;
an information obtaining system for obtaining ophthalmic information of the eye under test;
an inducing system having an optical system for projecting a visual target presented to the eye under test when the ophthalmic information is obtained, a focus condition of said optical system with respect to the visual target being variable; and
adjusting means for adjusting the focus condition of said optical system with respect to the visual target on the basis of the lens refractive power stored in said memory means.

* * * * *

UNITED STATES PATENT AND TRADEMARK OFFICE
CERTIFICATE OF CORRECTION

PATENT NO. : 5,270,749
DATED : December 14, 1993
INVENTOR(S) : TOSHIAKI OKUMURA

It is certified that error appears in the above-indentified patent and that said Letters Patent is hereby corrected as shown below:

On the Title Page
<u>AT [54]</u>
In the Title, "opthalmic" should read --ophthalmic--.

<u>COLUMN 1</u>
line 1, "opthalmic" should read --ophthalmic--.
line 19, "a" should read --an--.
line 39, "a" should read --the--.

<u>COLUMN 2</u>
line 38, "dichronic" should read --dichroic--.

<u>COLUMN 3</u>
line 5, "refractometering" should read --refractometer --.
line 30, "test" should read --test.--.
line 59, "put" should read --put on--.

<u>COLUMN 5</u>
line 31, "claim 1" should read --claim 1,--.
line 34, "claim 1" should read --claim 1,--.

Signed and Sealed this

Twelfth Day of July, 1994

Attest:

BRUCE LEHMAN

*Attesting Officer*     *Commissioner of Patents and Trademarks*